(12) United States Patent
Osakada et al.

(10) Patent No.: US 7,435,567 B2
(45) Date of Patent: Oct. 14, 2008

(54) METHOD FOR DEGRADATION OF NUCLEIC ACIDS AND USE THEREOF

(75) Inventors: Fumio Osakada, Okayama (JP); Yoshifumi Yanagida, Akashi (JP); Yasuyoshi Ueda, Himeji (JP)

(73) Assignee: Kaneka Corporation, Osaka (JP)

( * ) Notice: Subject to any disclaimer, the term of this patent is extended or adjusted under 35 U.S.C. 154(b) by 236 days.

(21) Appl. No.: 11/070,083

(22) Filed: Mar. 3, 2005

(65) Prior Publication Data

US 2005/0196827 A1 Sep. 8, 2005

Related U.S. Application Data (60) Provisional application No. 60/551,340, filed on Mar. 10, 2004.

(30) Foreign Application Priority Data

Mar. 4, 2004 (JP) .............................. 2004-061290

(51) Int. Cl.
*C12P 7/62* (2006.01)
(52) U.S. Cl. ..................................... 435/135
(58) Field of Classification Search .................. 435/135
See application file for complete search history.

(56) References Cited

U.S. PATENT DOCUMENTS

| 4,477,655 | A |  | 10/1984 | Holmes |  |
|---|---|---|---|---|---|
| 4,910,145 | A |  | 3/1990 | Holmes et al. |  |
| 5,110,980 | A |  | 5/1992 | Ramsay et al. |  |
| 5,977,250 | A | * | 11/1999 | George et al. | 524/845 |
| 6,808,907 | B2 | * | 10/2004 | Honma et al. | 435/135 |
| 2003/0032151 | A1 |  | 2/2003 | Honma et al. |  |
| 2007/0020739 | A1 | * | 1/2007 | Yokomizo | 435/135 |

FOREIGN PATENT DOCUMENTS

| JP | 58 212792 | 10/1984 |
|---|---|---|
| JP | 4 61638 | 10/1992 |
| JP | 7 31487 | 2/1995 |
| JP | 7 31488 | 2/1995 |
| JP | 7 31489 | 2/1995 |
| JP | 8 502415 | 3/1996 |
| JP | 11 266891 | 10/1999 |
| JP | 2002-125655 | 5/2002 |
| JP | 2002-253285 | 9/2002 |
| JP | 2003-12778 | 1/2003 |
| JP | 2003-47495 | 2/2003 |
| WO | WO 94/10289 | 5/1994 |

OTHER PUBLICATIONS

Williamson et al., "The isolation and estimation of the Poly-B-hydroxy butyrate inclusions by Bacillus Species" J. gen. Microbio. 19, 198-209 (1958).*
Roh, K.S., et al., "The effects of sodium bisulfite in extraction of PHB by hypochlorite," *Biotechnology Techniques*, vol. 9, No. 10, Oct. 1995, pp. 709-712.

* cited by examiner

*Primary Examiner*—Herbert J. Lilling
(74) *Attorney, Agent, or Firm*—Kenyon & Kenyon LLP (57) ABSTRACT

The present invention provides a method to efficiently degrade nucleic acids, which result in a viscosity increase of the solution thereof on the occasion of decomposition or solubilization of microbial cells, in an easy and simple manner in the step of recovering various useful substance produced by a microorganism, and a use thereof. The product recovery method of the present invention make the product recovery from within microbial cells with ease under relatively mild conditions, because, by bringing living microbial cells into contact with a little amount of hypochlorous acid or a salt thereof, autodigestion of nucleic acids is induced and following decomposition of microbial cells or viscosity increase of the solution thereof after dissolution is inhibited. The method of the present invention is particularly preferred in recovering polyhydroxyalkanoates, which are biodegradable polymers, from microbial cells.

22 Claims, 1 Drawing Sheet

METHOD FOR DEGRADATION OF NUCLEIC ACIDS AND USE THEREOF

This application claims priority to Japanese Patent Application No. 2004-061290 filed 4 Mar. 2004 and to U.S. Provisional Application No. 60/551,340 filed 10 Mar. 2004, the contents of which are incorporated herein by reference.

TECHNICAL FIELD

The present invention relates to a method for effective degradation of nucleic acids of a microorganism and facilitating the recovery of a useful substance produced by the microorganism, and to a use thereof.

BACKGROUND ART

In recent years, various important products have been produced on a commercial scale using microorganisms or recombinant microorganisms. In many cases, those products are produced and accumulated within microbial cells and, for recovering them, a step of decomposing or lysing the microbial cells is generally required. One of the problems encountered in this step is that when cells are decomposed or lysed, the viscosity of the solution increases as a result of extracellular liberation of nucleic acids. When released into a solution, nucleic acids get unfolded and form a network structure. This causes a marked increase in the viscosity of the cell lysation product and, for example, the whole solution becomes a gel and, accordingly, the solid/liquid separation becomes very difficult to make. Thus, the nucleic acid-induced viscosity increase can become a serious problem in the step of product recovery.

In the art, attempts have so far been made to chemically or physically degrade or degrade nucleic acids.

As for the method of chemically treating microbial cells (hereinafter sometimes referred to also as "microbes" or "cells"), U.S. Pat. No. 5,110,980 discloses a method of product recovery which comprises treating a suspension of cells with a large amount of hypochlorous acid to thereby chemically decompose and solubilize cell-constituting components other than the desired product. Although this method enables efficient degradation of nucleic acids, it is necessary, for obtaining a highly pure product, to carry out the hypochlorous acid treatment at a microorganism concentration of only 1%. Therefore, a large amount of hypochlorous acid is required and, further, the odor of chlorine remains in the product and a reduction is caused in molecular weight of the product; hence, this method is not suited for practical use.

In Japanese Kokai Publication Sho-58-212792, sodium hypochlorite is presented as a substance inducing autodigestion of cell walls, not nucleic acids. However, there is no detailed description or example of the relevant invention, hence the invention can hardly be said to have been completed.

Japanese Kohyo Publication Hei-08-502415 discloses a method comprising degradation of nucleic acids liberated upon surfactant treatment of cells with a peroxide. At room temperature, it takes 16 hours to chemically degrade those nucleic acids using hydrogen peroxide as the peroxide. The amounts of the surfactant and hydrogen peroxide are relatively large. Accordingly, this method is disadvantageous from the industrial production viewpoint.

Japanese Kokoku Publication Hei-04-61638 shows a recovery method according to which heat treatment is used in combination with an enzyme and a surfactant. This method is a method of recovering a polyhydroxyalkanoate (hereinafter referred to as "PHA" for short) which comprises preliminarily heating a microbial cell suspension at 100° C. or above to degrade nucleic acids and then decomposing cell constituents other than the PHA using any of various enzymes, followed by PHA recovery. However, the molecular weight of the PHA is markedly reduced upon heating at 100° C. or above, so that the product obtained is no longer suited for practical use.

In addition, there are the following methods of disrupting cells disclosed: the method comprising heating a PHA-containing microbial cell suspension at 50° C. or above under strong acidity conditions, namely at a pH below 2, followed by PHA separation (Japanese Kokai Publication Hei-11-266891), the method comprising adding an alkali to cells, then heating the resulting mixture at 80° C. and, after 1 hour of stirring, recovering the polymer by centrifugation (Japanese Kokai Publication Hei-07-31487), the method comprising carrying out high pressure disruption at 70° C. (Japanese Kokai Publication Hei-07-31488), and the method comprising adding an alkali and then carrying out high pressure disruption at 70° C. or above (Japanese Kokai Publication Hei-07-31489). While these methods cause disruption of nucleic acids as well, the acid, alkali, temperature and other conditions are severe, so that there arises the possibility of the decomposition of the product proceeding.

Thus, it is to be understood that, in product recovery from cells after cultivation, it is very difficult to efficiently disrupt nucleic acids in microbial cells without causing the product to be decomposed. Therefore, any process involving cell decomposition or lysis requires an effective method for degradation of nucleic acids so that the subsequent product recovery step may be carried out effectively or actually perfectly.

EXPLANATION OF SYMBOLS

1—Cell disrupter
2—Stirring apparatus
3—pH detection and control device
4—Pump
5—Pipe
6—pH adjusting agent reservoir
7—pH meter
8—Pipe
9—Disruption device
10—Pump
11—Cell disrupting vessel (constant-temperature bath circulator maintained at a low temperature)

DETAILED DESCRIPTION OF THE INVENTION

Accordingly, it is an object of the present invention is to provide a method for degradation of nucleic acids, which cause an increase in the viscosity of the solution upon decomposition or lysis of microbial cells, efficiently and in a simple and easy manner in using microorganisms and recovering various useful substances produced by the microorganisms as well as a use thereof.

As a result of intensive investigations made by them to accomplish the above object, the present inventors unexpectedly found for the first time that when living microorganisms after completion of cultivation are brought into contact with a small amount of hypochlorous acid or a salt thereof, autodigestion of nucleic acids occurs and the increase in solution viscosity in the subsequent step of cell decomposition or lysis is inhibited, so that the intracellular product can be recovered with ease under relatively mild conditions. Based on such and other findings, the present invention has now been completed.

Thus, the present invention provides a product recovering method which comprises, in the step of recovering a substance produced by a microorganism from within microbial cells, bringing living microbial cells into contact with an amount appropriate for induction of autodigestion of nucleic acids of hypochlorous acid or a salt thereof and then carrying out the step of product recovery.

The product recovering method the invention preferably comprises bringing living microbial cells into contact with hypochlorous acid or a salt thereof in an effective chlorine concentration of 0.3 to 14% by weight relative to dried microbial cells for 10 minutes to 5 hours to thereby cause autodigestion of nucleic acids and then disrupting or lysing the microbial cells for product recovery. The method of the invention is most preferably used in recovering polyhydroxyalkanoates, which are biodegradable polymers, from microbial cells.

In the following, the present invention is described in detail.

The hypochlorous acid or salt thereof to be used in the practice of the invention is commercially available as sodium hypochlorite or calcium hypochlorite (bleaching powder). Among these, sodium hypochlorite is preferably used because of its low cost and its stability upon dissolution in water.

For judging as to whether the degradation of nucleic acids in cells is complete or not in the practice of the invention, it is simply only necessary to lyse the microbial cells with an alkali, followed by viscosity checking. In case of insufficient nucleic acid degradation, the remaining nucleic acids are released upon alkaline lysis, with the result that the cell suspension becomes gel-like and the fluidity thereof is lost. When the degradation of nucleic acids is complete, the suspension retains its fluidity even after addition of an alkali. Both the cases thus can be distinguished with ease. In a large-scale experiment, viscosity measurement using a viscometer, for instance, will be helpful.

When living cells (hereinafter sometimes also referred to as "viable cells") after cultivation are treated by contacting them with an amount appropriate for inducing autodigestion of nucleic acids of hypochlorous acid or a salt thereof and then an alkali is added thereto, the cell suspension retains fluidity, indicating that the nucleic acids have been degraded. After sterilization of viable cells by heating, however, the treatment of the cells with hypochlorous acid or a salt thereof in the same manner and the subsequent addition of an alkali give a highly viscous gel. This indicates that the treatment with hypochlorous acid or a salt thereof is effective only against viable cells.

After completion of the treatment of viable cells with hypochlorous acid or a salt thereof, observation of the cells under a microscope does not reveal any sign of lysis but the cells retain the same shape as the viable cells. Thus, supposedly, the contacting with hypochlorous acid or a salt thereof will not result in disruption of cell walls, cell membranes, insoluble proteins and the like. Accordingly, it is suggested that hypochlorous acid or a salt thereof does not directly act on nucleic acids to chemically degrade them but indirectly induces nucleic acid degradation (autodigestion).

In the practice of the invention, it is necessary to treat cells in the state of viable cells with hypochlorous acid or a salt thereof without treating the cells for sterilization by heat treatment or treatment with an alkali or acid. The hypochlorous acid or a salt thereof may be added directly to the culture fluid after cultivation of the microorganism or may be added to the cells recovered by such a method as centrifugation or membrane separation.

In an embodiment of the present invention, the concentration of hypochlorous acid or a salt thereof is not particularly restricted provided that it is appropriate for inducing autodigestion of nucleic acids. In the present invention, the concentration of hypochlorous acid or a salt thereof is given herein in terms of effective chlorine concentration. The effective chlorine concentration is the concentration of chlorine (Cl2) generated upon addition of an acid to hypochlorous acid or a salt thereof. In the following, the concentration of hypochlorous acid or a salt thereof is given as the percentage by weight thereof as expressed in terms of effective chlorine concentration per unit weight (g) of dried cells. The concentration applicable is thought to vary depending on the microbial species and may be determined according to the microorganism to be used.

Generally, the concentration of hypochlorous acid or a salt thereof is preferably not lower than 0.3% by weight, more preferably not lower than 0.4% by weight, most preferably not lower than 0.5% by weight so that nucleic acid degradation may be induced more reliably. As for the upper limit to the concentration of hypochlorous acid or a salt thereof, it is preferably not higher than 14% by weight, more preferably not higher than 10% by weight, since a higher concentration will lead to cell death; when economical inexpensiveness is further taken into consideration, the upper limit is most preferably not higher than 8% by weight. Sodium hypochlorite, for instance, is available in the form of an aqueous solution and, commercially, it is supplied as a solution having an effective chlorine concentration of 12% by weight.

The concentration of hypochlorous acid or a salt thereof is to be determined depending on the amount of the microorganism, hence is not restricted by the concentration of the microorganism in the solution.

Unlike the chemical dissolution or decomposition of microbial cells (U.S. Pat. No. 5,110,980, Japanese Kokai Publication Sho-58-212792, Japanese Kohyo Publication Hei-08-502415), the method of the present invention can be carried out at a relatively high microorganism concentration. Considering the effect of treatment with hypochlorous acid or a salt thereof, the microorganism concentration on the dried cell basis is preferably not lower than 3% by weight, more preferably not lower than 5% by weight, most preferably not lower than 8% by weight. The upper limit is preferably not higher than 50% by weight, more preferably not higher than 40% by weight, most preferably not higher than 30% by weight; the only requirement is that viable cells can be stirred sufficiently.

For efficient nuclease induction and nucleic acid autodigestion, the time of contact between microbial cells and hypochlorous acid or a salt thereof is preferably not shorter than 10 minutes, more preferably not shorter than 20 minutes, still more preferably not shorter than 30 minutes. Considering the possibility of the product being decomposed as a result of induction of some product-decomposing enzyme being induced, the upper limit to the treatment time is preferably not longer than 5 hours, more preferably not longer than 3 hours, most preferably not longer than 2 hours.

The autodigestion-inducing temperature is preferably that temperature which is the optimum growth (cultivation) temperature for the microorganism used. Generally speaking, the optimum growth temperature is preferably within the range of about 15° C. to 40° C., although it may vary according to the species of microorganism. In the case of *Alcaligenes eutrophus*, for instance, a temperature of about 20° C. to 35° C. is preferred; in the case of *Escherichia coli*, about 20° C. to 37° C.; and, in the case of yeasts, about 25° C. to 37° C.

The pH at which autodigestion is to be induced by bringing microbial cells with hypochlorous acid or a salt thereof is preferably that pH which is the optimum growth (cultivation) pH for the microorganism used. Generally, the pH range of 4 to 8 is preferred. In the case of *Escherichia coli*, for instance, a pH of 5 to 7 is preferred; in the case of *Alcaligenes eutrophus*, a pH of 5 to 7; and, in the case of yeasts, a pH of 4 to 7. Neither hypochlorous acid nor salts thereof correspond to those peroxides disclosed in Japanese Kohyo Publication Hei-08-502415.

In practicing the method of the invention, the microbial product is not particularly restricted but includes, for example, polyhydroxyalkanoates (PHAs), proteins, antibiotics, lipids, carbohydrates and the like. The present invention, however, is especially useful in cases where the microbial product is a PHA, which is a biodegradable polymer.

In a preferred embodiment of the invention, the hydroxyalkanoate unit of the PHA is not particularly restricted but specifically includes 3-hydroxybutyrate (3HB), 3-hydroxyvalerate (3HV), 3-hydroxypropionate, 4-hydroxybutyrate, 4-hydroxyvalerate, 5-hydroxyvalerate, 3-hydoxyhexanoate (3HH), 3-hydroxyheptanoate, 3-hydoxyoctanoate, 3-hydroxynonanoate, 3-hydroxydecanoate and the like. In the practice of the invention, the polyhydroxyalkanoate may be a homopolymer of such a hydroxyalkanoate or a copolymer resulting from copolymerization of two or more hydroxyalkanoate species. Preferably, it is a copolymer resulting from copolymerization of two or more species.

As specific examples of the PHA, there may be mentioned PHB, which is a homopolymer of 3HB, PHBV, which is a binary copolymer of 3HB and 3HV, PHBH, which is a binary copolymer of 3HB and 3HH (cf. Japanese Patent No. 2,777, 757), and PHBHV, which is a ternary copolymer of 3HB, 3HV and 3HH (cf. Japanese Patent No. 2,777,757), and the like. In particular, 3HH-containing copolymers are preferred because of their having degradability as biodegradable polymers and their being soft. More preferred is PHBH.

In the case of PHBH, the proportions of the respective constituent monomer units are not particularly restricted but, preferably, the 3HH unit content is not higher than 40 mole percent, more preferably not higher than 30 mole percent, most preferably not higher than 20 mole percent. In the case of PHBHV, the proportions of the respective constituent monomer units are not particularly restricted but, preferably, the 3HB unit content is, for example, within the range of 1 to 95 mole percent, the 3HV unit content in the range of 1 to 96 mole percent, and the 3HH unit content in the range of 1 to 30 mole percent.

For a PHA to be suited for practical use, the PHA must have a weight average molecular weight of not lower than 10,000 as determined by gel chromatography using polystyrene species as molecular weight standards. As a matter of course, the molecular weight applicable may vary according to a variety of uses. Considering the molecular weight reductions in the pelletizing and later processing steps, however, the PHA recovered in accordance with the present invention and dried should have a weight average molecular weight of preferably not lower than 200,000, more preferably not lower than 300,000, most preferably not lower than 400,000.

In a preferred embodiment of the invention, the microorganism to be used in the practice of the invention is preferably an organism capable of containing a PHA within cells. For example, when the cultivation conditions are adjusted, microorganisms of the genus *Alcaligenes*, such as *Alcaligenes lipolytica* and *Alcaligenes latus*, of the genus *Ralstonia*, such as *Ralstonia eutropha*, of the genus *Pseudomonas*, such as *Pseudomonas oleovorance* and *Pseudomonas resinovorans*, of the genus *Bacillus*, of the genus *Azotobacter*, of the genus *Nocardia*, such as *Nocardia salmonicolur*, of the genus *Aeromonas*, such as *Aeromonas caviae*, of the genus *Rhodospirillum*, such as *Rhodospirillum rubrum*, of the genus *Zoogloea*, such as *Zoogloea ramigera*, of the genus *Methylobacterium*, of the genus *Paracoccus*, of the genus *Clostridium*, of the genus *Halobacterium*, of the genus *Candida*, of the genus *Saccharomyces*, and of the genus *Yarrowia*, among others, can accumulate a PHA within cells. Preferred as the microorganism is *Aeromonas caviae*.

The microorganism to be used in the practice of the invention may be a transformant resulting from introduction of a gene group involved in PHA synthesis in such a microorganism as mentioned above. In that case, the host is not particularly restricted but includes the microorganisms mentioned above and, further, *Escherichia coli* and yeasts (cf. WO 01/88144), and the like. Preferred among them are *Aeromonas caviae*, and transformant cells produced by introduction of the PHA synthetase group genes of *A. caviae* since they are capable of synthesizing PHBH, which is an excellent biodegradable polymer. In particular, *Ralstonia eutropha* with the PHA synthetase group genes of *A. caviae* introduced therein is more preferred, and an example of such microorganism has been internationally deposited with the National Institute of Advanced Industrial Science and Technology, Central 6, 1-1-1 Higashi, Tsukuba, Ibaraki, Japan, under the Budapest Treaty under the name *Alcaligenes eutrophus* AC32 (deposited: Aug. 7, 1997); accession number: FERM BP-6038).

The method of cultivating the PHA-containing microorganisms enumerated herein is not particularly restricted but, for example, the method shown in Japanese Kokai Publication 2001-340078 and well known in the art may be used.

When the microbial product is a PHA, the method of the present invention is preferably such that the product recovery process to be carried out after bringing living cells with an amount appropriate for inducing autodigestion of nucleic acids of hypochlorous acid or a salt thereof comprises the following steps (a) and (b):

(a) The step of adding an alkali to an aqueous suspension of PHA-containing microbial cells while stirring and carrying out a physical disruption treatment to thereby disrupt the cells and, at the same time, solubilize or emulsify cell substances other than the PHA in those cells and then separating the PHA from the suspension;

(b) The step of treating the PHA separated with an enzyme and/or a surfactant to solubilize or digest and then solubilize impurities adhering to the PHA and then washing the PHA with a hydrophilic solvent and/or water.

Thus, in a preferred embodiment of the invention, in recovering the polymer in question from PHA-containing microbial cells, the step (a) can be followed after autodigestion of nucleic acids by treatment with hypochlorous acid or a salt thereof. In the step (a) in accordance with the invention, it is important to add an alkali to an aqueous suspension of PHA-containing microbial cells while stirring and treating the aqueous suspension of PHA-containing microbial cells for physical disruption. Thus, in reality, the step comprises the process consisting in (1) preparing an aqueous suspension of PHA-containing microbial cells, (2) initiating first the physical disruption treatment while stirring the aqueous suspension, and (3) adding then an alkali while continuing the stirring and physical disruption treatment.

The method of stirring the aqueous suspension in the step of adding an alkali is not particularly restricted but preferably comprises stirring using an emulsifying/dispersing apparatus, an ultrasonic disrupter or the like so that the alkali may be efficiently diffused and insoluble substances other than the polymer as discharged from cells may efficiently be disrupted. More preferably, an emulsifying/dispersing apparatus is used; such apparatus includes, but is not limited to, Silverson mixer (product of Silverson Machines Inc., England), Clearmix (product of MTEC Co., Ltd., Japan), and Ebaramilder (product of Ebara Corp., Japan), and the like.

The apparatus to be used in the step (a) for physical disruption treatment is not particularly restricted but includes high-pressure homogenizers, ultrasonic disrupters, emulsifying/dispersing apparatus, bead mills and the like. Among them, high-pressure homogenizers are preferred, and that type of such homogenizer in which an aqueous suspension of microbial cells is introduced into a pressure vessel having a minute opening and forced out through the opening under high pressure is more preferred. High-pressure homogenizers produced by Niro Soavi S.p.A. (Italy) are preferably used as such apparatus comprising a pressure vessel and a pressurizing mechanism. Other ones employable include, but are not limited to, Bran-Luebbe continuous cell disrupters (products of Bran+Luebbe, Germany) and Microfluidizer processors (products of Microfluidics Corp., USA), and the like.

In such a high-pressure homogenizer, a great shearing force is exerted on microbial cells, so that the cells are efficiently disrupted and PHA separation is promoted. In that apparatus, a high pressure is exerted on the cell suspension at the opening and the temperature momentarily rises. Since the polymers in question are readily decomposable at elevated temperatures and, therefore, the aqueous suspension is preferably cooled in an ordinary constant temperature bath circulator maintained at a low temperature to inhibit the temperature from rising during processing. A preferred disruption pressure is not lower than 300 kgf/cm$^2$, more preferably not lower than 400 kgf/cm$^2$.

The present inventors found that when, on the occasion of PHA recovery, the pH of the suspension is adjusted in advance to 10 or above by addition of an alkali and then subjected to physical disruption (e.g. cell disruption and emulsification using a high-pressure homogenizer), PHA decomposition readily occurs and, conversely, when physical disruption is carried out before addition of the alkali, unexpectedly, PHA decomposition hardly occurs. In this case, however, when undigested nucleic acids were present, the undigested nucleic acids caused an increase in viscosity and, therefore, for facilitating the PHA recovery, it was necessary to disrupt nucleic acids many times over a long period of time while adding the alkali gradually and avoiding any abrupt increase in viscosity. Thus, in the case of production on a commercial scale, the polymer recovery step requires a long period of time. For increasing the output, it was necessary to increase the number of disrupters. On the contrary, when the nucleic acid autodigestion method of the present invention is employed, the time required for physical disruption can be markedly reduced and, therefore, it is evident that the number of disrupters can be reduced and, as a result, the product cost can be reduced.

In the step (a), the physical disruption is preferably metal hydroxides such as barium hydroxide; and aqueous ammonia; and the like. These may be used singly or two or more of them maybe used in combination. Among them, alkali metal hydroxides and alkali metal carbonates are preferred, and sodium hydroxide, potassium hydroxide, lithium hydroxide and sodium carbonate are more preferred, in view of their being fitted for commercial production and their cost.

In the step (a), the separation of the PHA from the aqueous suspension can be made, for example, by centrifugation, membrane separation, filter filtration or the like.

In the practice of the invention, the PHA obtained after the step (a) can also be recovered as an emulsion.

In the following, referring to FIG. 1, which is a schematic representation of a preferred apparatus for carrying out the step (a), the step (a) is described in more detail. As a matter of course, such an apparatus example is by no means limitative of the scope of the present invention.

Figure 1:
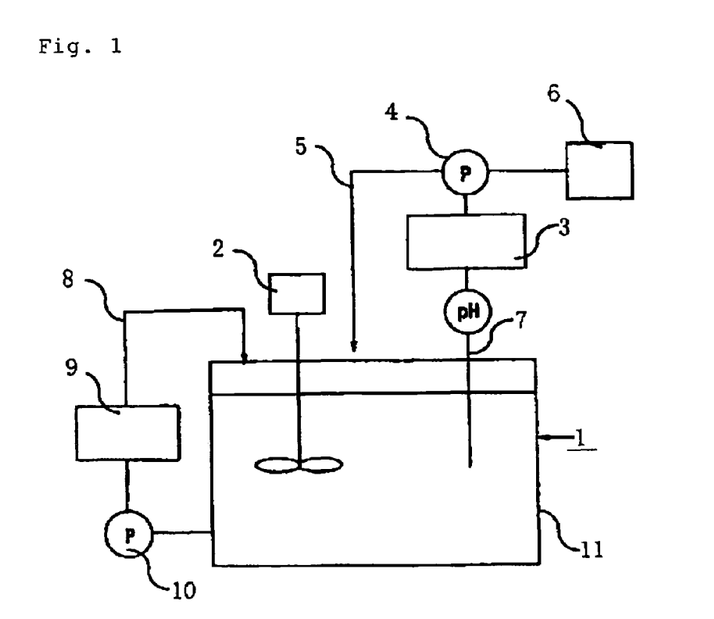
FIG. 1 is an explanatory drawing of a cell disrupting apparatus for carrying out the PHA separation purification method according to the invention.

In FIG. 1, the reference numeral 1 indicates a cell disrupter as a whole to be used in the practice of the invention. The numeral 6 indicates a pH adjusting agent reservoir for reserving an alkaline chemical, and the chemical in the pH adjusting agent reservoir 6 is fed to a cell disrupting vessel 11 via a pipe 5 by means of a pump 4 to adjust the pH of the aqueous suspension of microbial cells in the cell disrupting vessel 11 according to need. Further, the cell disrupting vessel 11 is equipped with a stirring apparatus 2 for uniformly stirring and mixing the pH adjusting agent fed from the pH adjusting agent reservoir 6 with the aqueous suspension of microbial cells in the cell disrupting vessel 11. In the cell disrupting vessel 11, there is also provided a pH detection and control means constituted of a pH meter 7 and a pH detection and control device 3 so that the pH of the microbial cell suspension in the cell disrupting vessel 11 may be detected and the rate of feeding by the pump 4 may be controlled for adjustment to the predetermined pH. Here, the cell disrupting vessel 11 molecular weight of the PHA can be prevented, so that the decrease is not larger than 15% as compared with the product obtained after cultivation. When a high-pressure homogenizer is used in physical disruption treatment, the treatment is to be carried out while cooling the cell suspension using a constant temperature bath circulator maintained at a low temperature, as described above. When microbial cells are disrupted in such an adequate alkaline environment, results with good reproducibility can be obtained.

In the step (a), the aqueous suspension can be prepared by suspending, in an aqueous medium, the PHA-containing microbial cells after contacting with hypochlorous acid or a salt thereof. The culture fluid after bringing microbial cells with hypochlorous acid or a salt thereof may be used either as such or after further concentration or dilution. The concentration of cells in the aqueous suspension is preferably not higher than 500 g expressed in terms of dried cells per liter of the aqueous suspension. From the viewpoint of the ease of stirring of the aqueous suspension, the concentration is more preferably not higher than 300 g. A preferred lower limit is 80 g or above.

The alkali to be used in the step (a) is not particularly restricted but may be any of those capable of destructing the cell wall of the PHA-containing microorganism and extracellularly discharging the PHA occurring in the cells. Thus, the alkali includes, but is not limited to, alkali metal hydroxides such as sodium hydroxide, potassium hydroxide and lithium hydroxide; alkali metal carbonates such as sodium carbonate and potassium carbonate; alkali metal hydrogen carbonates such as sodium hydrogen carbonate and potassium hydrogen carbonate; alkali metal salts of organic acids, such as sodium acetate and potassium acetate; alkali metal borates such as borax; alkali metal phosphates such as trisodium phosphate, disodium hydrogen phosphate, tripotassium phosphate and dipotassium hydrogen phosphate; alkaline earth carried out while controlling the pH of the aqueous suspension to 9 to 13.5, and the pH is preferably controlled on the occasion of addition of the alkali. The pH range in which cell-derived insoluble substances (cell substances) other than the desired PHA can be more effectively solubilized or emulsified while any significant adverse effect will not be produced on the PHA itself is pH 9 to 13.5, and a more preferred lower limit is pH 10 and a more preferred upper limit is pH 13. AtpH levels above 13.5, the molecular weight of the PHA tends to be reduced and, at pH levels below 9, the disruption effect will be unsatisfactory.

In the step (a), after treatment with hypochlorous acid or a salt thereof, the pH is preferably adjusted to a predetermined level by adding an alkali gradually or stepwise while carrying out the physical disruption of cells, and the physical disruption is then continued. In particular, the method comprising carrying out physical disruption of the whole amount of cells at least once, then adjusting the pH to an arbitrary level between pH 9 to 13.5 by addition of an alkali while stirring the aqueous suspension and continuing the physical disruption while controlling the pH is more preferred. By doing so, it becomes possible to realize the solubilization or emulsification of insoluble substances (cell substances) other than the PHA in a shorter period of time and separate and recover the PHA from the aqueous suspension with ease without causing any substantial decomposition of the PHA.

For effectively inhibiting the PHA from decreasing in molecular weight, the temperature at which the step (a) is to be carried out is preferably 10 to 45° C., more preferably 20 to 40°. In the practice of the invention, the pH is controlled to prevent the pH from becoming excessively high and, at the same time, always maintain the pH at an arbitrary level between pH 9 and 13.5, whereby insoluble proteins can be maintained in a solubilized state, so that it is not necessary to raise the temperature of the suspension; as a result, the decrease in serves also as a constant temperature bath circulator maintained at a low temperature, so that the aqueous suspension of microbial cells can be maintained constant at a desired temperature.

Referring to FIG. 1, the aqueous suspension of microbial cells in the cell disrupting vessel 11 is fed to a disruption device 9 via a pump 10 and, after efficient disruption of undigested nucleic acids, which cause a viscosity increase, in the disruption device 9, returned to the cell disrupting vessel 11 via a pipe 8. By the stirring apparatus 2, the alkali added is rapidly diffused and the aqueous suspension of microbial cells becomes uniform and, thus, the pH of the aqueous suspension of microbial cells can be adjusted strictly. To avoid the alkali concentration locally becoming excessively high to cause hydrolysis of the polymer, stirring is preferably carried out to a sufficient extent. The target range of pH control is preferably narrower by 1, more preferably by 0.5, from the predetermined upper and lower limits, respectively. Thus, the pH is preferably controlled so that it may fall within the pH range of 9 to 13.5, including such upper and lower margins.

Employable as the disruption device 9 are such apparatus as high-pressure homogenizers, ultrasonic disrupters, emulsifying/dispersing apparatus, bead mills and the like, as described hereinabove. Two or more disruption devices, which may be the same or different in type, may be disposed either in parallel or in series. Preferably used as the stirring apparatus 2 are such emulsifying/dispersing apparatus and ultrasonic disrupters so that the alkali added may be diffused efficiently and undigested nucleic acids and cell walls discharged from cells and other insoluble substances, and the like, may be disrupted efficiently. In-line mixer type ones are also available as such apparatus and, for example, they each can serve simultaneously as the pump 10 and as the stirring apparatus 2 shown in FIG. 1. In this case, the structure can advantageously be simplified. The pH meter 7 and pH detection and control device 3 to be used may be general-purpose ones.

In the practice of the invention, when the relatively low purity PHA obtained in the step (a) is subjected to the treatment in the step (b), such remarkable effects as described later herein can be obtained. Presumably, small amounts of proteins, cell wall-constituting peptidoglycan, lipids, polysaccharides, nucleic acids and other carbohydrates are sticking to the PHA particles obtained in the step (a). In the step (b) in accordance with the present invention, the treatment can be carried out for the purpose of removing at least some of the above adhering components to increase the purity of the PHA.

Thus, the step (b) consists in a PHA purification process comprising solubilizing or decomposing and solubilizing impurities adhering to the PHA using either an enzyme or a surfactant, or both in combination.

To further enhancing the effects of the treatment in step (b) in the practice of the invention, the PHA separated in the step (a) is not used in a dried form but preferably is used in the form of a suspension of the PHA separated in the step (a) in water as it is or in the form wet with water as obtained after separation/recovery by centrifugation or membrane separation, for instance, to be used in the following step (b).

In cases where the treatment in the step (b) is carried out using an enzyme, the enzyme to be used includes proteases, fatty acid decomposing enzymes, cell wall decomposing enzymes and nucleases, and the like. These may be used singly or two or more species may be used in combination. Specific examples of these enzymes are as follows. As the proteases, there may be mentioned Alcalase, pepsin, trypsin, papain, chymotrypsin, aminopeptidases, carboxypeptidases, and the like. As the carboxylic acid decomposing enzymes, there may be mentioned lipases, phospholipases, choline esterases, phosphatases, and the like. As the cell wall decomposing enzymes, there may be mentioned lysozyme, amylases, cellulases, maltase, saccharase, $\alpha$- and $\beta$-glycosidase, and the like. As the nucleases, there may be mentioned ribonucleases and the like. These may be used singly or two or more species may be used in combination.

The enzymes utilizable in this step are not limited to those enumerated above but any arbitrary one of those enzymes which can be used in producing commercial products. Those enzyme-containing laundry detergents which are generally available on the market can also be used. Not only enzymes but also enzyme compositions containing an enzyme(s) together with an enzyme stabilizer and/or a recontamination inhibitor may be used as well.

For the purpose of decomposing and eliminating insoluble proteins adhering to the PHA or insoluble cell wall debris, in particular, at least one species selected from among proteases and cell wall decomposing enzymes is preferred, and the use of one or more proteases is more preferred. As preferred proteases included among the examples given above, there may be mentioned such industrially usable ones as Protease A, Protease P, Protease N (all the three being product names; products of Amano Enzyme Inc.), Alcalase, Savinase and Everlase (the three being product names; products of Novozymes A/S), and the like. These are judiciously used from the decomposing activity viewpoint as well. As a preferred cell wall decomposing enzyme, there maybe mentioned lysozyme among those examples given above. The enzyme to be used is not limited to these, however.

As for the temperature at which the enzymatic treatment is carried out, the optimum temperature for the enzyme selected is of course preferred. Since the molecular weight of the PHA will decrease at high temperatures, an upper limit of 50° C. or below is preferred. A preferred lower limit is generally 20° C. or above. The enzyme treatment is preferably carried out until a desired extent of treatment is attained, and the time therefor is generally 0.5 to 2 hours. The usage of the enzyme depends on the enzyme species and the activity thereof but is not particularly restricted. Preferably, the usage is 0.001 to 10% by weight relative to the polymer weight and, from the cost viewpoint, an usage of 0.001 to 5% by weight is more preferred.

As compared with the conventional method (Japanese Kokoku Publication Hei-04-61638) comprising treating PHA-containing cells themselves with an enzyme and disrupting cells, the method of the present invention requires the use of an enzyme only in an amount sufficient to solubilize insoluble substances remaining in small amounts in the PHA and therefore is advantageous in that the PHA can be produced economically at low cost.

In the step (b), the enzyme treatment may also be carried out in two or more stages. For example, one enzyme is used in the first stage and then treatment may be carried out using the same enzyme or a different enzyme. In cases where two or more enzymes are used, it is convenient to treat the PHA in one stage using a mixture of those enzymes, if they will not digest with each other.

In the step (b) in accordance with the present invention, it is also possible to use a surfactant as a solubilizing agent for removing impurities adhering to PHA particles. The surfactant to be used in the practice of the invention may be an anionic surfactant, a cationic surfactant, an amphoteric surfactant, a nonionic surfactant and the like. The surfactant may comprise one single species or two or more species.

The anionic surfactant includes alkylsulfuric acid salts, alkylbenzenesulfonic acid salts, alkyl or alkenyl sulfuric acid ester salts, alkyl or alkenyl ether sulfuric acid ester salts, α-olefinsulfonic acid salts, fatty acid salts or esters thereof, α-sulfo-fatty acid salts or esters thereof, alkyl or alkenyl ether-carboxylic acid salts, amino acid type surfactants, N-acyl-amino acid type surfactants and the like. Preferred among them are alkylsulfuric acid salts whose alkyl moiety contains 12 to 14 carbon atoms, linear alkylbenzenesulfonic acid salts whose alkyl moiety contains 12 to 16 carbon atoms, and alkyl sulfuric acid ester salts and alkyl ether sulfuric acid ester salts whose alkyl ester contains 10 to 18 carbon atoms. The counter ion includes as preferred species, but is not limited to, alkali metals such as sodium and potassium, alkaline earth metals such as magnesium, and alkanolamines such as monoethanolamine, diethanolamine and triethanolamine.

The cationic surfactant includes alkyltrimethylammonium salts, dialkyldimethylammonium salts and the like.

The amphoteric surfactant includes carbobetaine type and sulfobetaine type surfactants, and the like.

The nonionic surfactant includes polyoxyalkylene (preferably polyoxyethylene) alkyl or alkenyl ethers, polyoxyalkylene (preferably polyoxyethylene) alkyl- or alkenylphenyl ethers, polyoxyethylenepolyoxypropylene alkyl or alkenyl ethers, polyoxyethylenepolyoxypropylene glycols, polyoxyethylene glycol, polyoxyethylenealkylamines, higher fatty acid alkanolamides, alkylglucosides, alkylglucosamides, alkylamine oxides, etc. Among them, highly hydrophilic ones and ones low or lacking in ability to form liquid crystals upon admixture with water are preferred, and polyoxyalkylene C10-14 alkyl ethers, polyoxyethylene glycol and the like are preferably used in view of their relatively good biodegradability. Preferred examples of the polyoxyalkylene C10-14 alkyl ethers include, but are not limited to, polyoxyethylene C10-14 alkyl ethers.

Specifically, among the surfactants mentioned above, the following are preferred from the cost, usage and/or effect-of-addition viewpoint: anionic surfactants such as sodium dodecyl sulfate, sodium dodecylbenzenesulfonate, sodium cholate, sodium deoxycholate and sodium oleate; and nonionic surfactants such as polyoxyethylene glycol, polyoxyethylene C10-14 alkyl ethers. The combined use of two or more of these is also preferred.

The surfactants mentioned above are used also in laundry detergents generally available on the market, and any of appropriate laundry detergents may be used as the surfactant in question.

From the detergency viewpoint, anionic surfactants and nonionic surfactants are preferred. The use of anionic surfactants is preferred for the purpose of washing out and removing proteins and the like, while the use of nonionic surfactants is preferred for the purpose of washing out and removing fatty acids, fats and oils or in the case of combined use of an enzyme. The surfactant to be used may comprise both of an anionic surfactant and a nonionic surfactant. When both are contained, the anionic surfactant/nonionic surfactant weight ratio is preferably 1/100 to 100/10, more preferably 5/100 to 100/20, still more preferably 5/100 to 100/100, most preferably 5/100 to 50/100.

The level of addition of the surfactant is not particularly restricted but preferably is 0.001 to 10% by weight based on the polymer weight and, from the cost viewpoint, 0.001 to 5% by weight is preferred.

The treatment temperature in the surfactant treatment is not particularly restricted but, from the viewpoint of promoting the solubilization of cell constituents other than the PHA, the range of 20 to 50° C. is preferred. A preferred treatment time is generally 0.5 to 2 hours.

As a preferred embodiment of the invention, there may be mentioned the combined use of an enzyme and a surfactant, since higher purification effects can be obtained then. When an enzyme and a surfactant are used in combination, the usage of the enzyme and the usage of the surfactant are respectively the same as mentioned above. In the case of such combined use, the treatment temperature is preferably 20 to 50° C., and the treatment time is preferably 0.5 to 2 hours. Both the enzyme treatment and surfactant treatment are preferably carried out with stirring.

The present inventors have noticed significant effects of the combined use of the two agents. The reason is presumably that the surfactant effectively remove those decomposition products liberated by enzymatic decomposition and rendered insoluble or that the proteins are modified in structure by the surfactant and becomes susceptible to enzymatic decomposition. In this case, while the surfactant and enzyme may be prepared separately and then used as an appropriate mixture, a commercially available enzyme-containing laundry detergent is a mixture of a surfactant and an enzyme and therefore it can also be used as such.

Which treatment, with an enzyme and/or a surfactant, is to be carried out in the step (b) in accordance with the invention can be properly selected according to such reasons and/or purposes as which impurity species are to be particularly eliminated, the cost, other process restrictions, and the desired purity of the PHA.

In the step (b) in accordance with the invention, the PHA particles obtained by the above-mentioned enzyme and/or surfactant treatment are preferably washed with a hydrophilic solvent and/or water for further elimination of impurities, namely for defatting, deodorization, decolorization and the like. This step makes it possible to isolate the PHA more improved in purity. The hydrophilic solvent to be used in this step is not particularly restricted but specifically includes methanol, ethanol, propanol, isopropanol, acetone, acetonitrile, tetrahydrofuran, etc. Among these hydrophilic solvents, methanol and ethanol are particularly preferred since they are economically inexpensive and excellent in detergency. The hydrophilic solvent may also be used in admixture with water. In cases where a mixed solvent composed of water and a hydrophilic solvent, the mixing ratio by volume (water/hydrophilic solvent) is preferably about 9.5/0.5 to 0.5/9.5. The amount of the solvent to be used for washing is not particularly restricted but preferably at least equal to the volume of the polymer. The temperature during washing is preferably not lower than 20° C. but lower than 60° C. Further, this washing step may be carried out using water alone.

In the practice of the invention, a high-purity PHA can be recovered after completion of this step (b) and it can be used as a molding material, and the like. In particular, the PHA at this point of time can form an emulsion comprising fine particles with an average particle size of 0.7 micron and therefore can be properly used in such a field of application as a paper coating material. The use thereof is not limited to this, however.

In a preferred embodiment of the invention, the PHA obtained in the step (b) occurs as fine particles with a particle size of several microns and, therefore, may be subjected to aggregation to an appropriate particle size in the following step (c) in view of separativity, workability and the like. (c) The step consisting in suspending the washed PHA in a hydrophilic solvent and/or water, stirring the suspension at a temperature not higher than the boiling point of the suspension to allow the PHA to aggregate to an increased particle size and then separating the PHA aggregates from the suspension.

The-step (c) according to the invention is a step of increasing the PHA particle diameter by causing PHA particles to aggregate by a simple and easy procedure comprising suspending the PHA purified in the step (b) in a hydrophilic solvent and/or water and stirring the suspension at a temperature not higher than the boiling point thereof.

The hydrophilic solvent to be used in the step (c) is not particularly restricted but includes, for examples, alcohols such as methanol, ethanol, 1-propanol, 2-propanol and butanol; ketones such as acetone and methyl ethyl ketone; ethers such as tetrahydrofuran and dioxane; nitriles such as acetonitrile and propionitrile; amides such as dimethylformamide and acetamide; dimethyl sulfoxide, pyridine, piperidine and the like. Among them, methanol, ethanol, 1-propanol, 2-propanol, butanol, acetone, methyl ethyl ketone, tetrahydrofuran, dioxane, acetonitrile, propionitrile and the like are preferred because of the good removability of such solvents. More preferred from the ready availability viewpoint are methanol, ethanol, 1-propanol, 2-propanol, butanol, acetone, tetrahydrofuran and acetonitrile. Still more preferred is the use of the solvent used in washing the PHA in the step (b), and this makes it possible to start the aggregation procedure continuedly and reduce the cost of equipment since only one solvent vessel is required. Therefore, methanol, ethanol, propanol, isopropanol, acetone, acetonitrile and tetrahydrofuran may be mentioned as more preferred solvents. Among them, methanol and ethanol, which are economically inexpensive and excellent in detergency, are particularly preferred.

The above-mentioned hydrophilic solvent may be used in admixture with water. Thus, the suspension may comprise, as the dispersion medium, a hydrophilic solvent alone, water alone or a mixed solvent composed of a hydrophilic solvent and water and preferably comprises a mixed solvent composed of a hydrophilic solvent and water. The concentration of the hydrophilic solvent in the mixed solvent is preferably not lower than 10% by weight, more preferably not lower than 20% by weight, so that a sufficient aggregating effect may be obtained. The upper limit of the hydrophilic solvent is preferably set at 99% by weight or below, more preferably at 98% by weight or below, still more preferably at 97% by weight or below.

The PHA concentration in the suspension in the step (c) is not particularly restricted but preferably is not lower than 1 g/L, more preferably not lower than 10 g/L, still more preferably not lower than 30 g/L. The upper limit is preferably 500 g/L or below, more preferably 300 g/L or below, still more preferably 200 g/L or below, so that the fluidity of the PHA suspension may be secured. The means of stirring in the step (c) according to the invention is not particularly restricted but, as such, there may be mentioned stirring vessels and like other turbulent flow-causing means. The temperature on the occasion of aggregation in the step (c) according to the invention is preferably room temperature (about 24° C.) or above, more preferably 40° C. or above, still more preferably 60° C. or above. The upper limit is not particularly restricted but any arbitrary temperature up to the boiling point of the suspension may be selected. The step (c) can be carried out either under ordinary pressure conditions or under high pressure conditions.

In the step (c) according to the invention, the desired aggregation can be caused to occur generally in a very short period of time, namely in about several minutes, and, therefore, if the PHA is isolated by filtration and the like, immediately after aggregation, there is no need of apprehension about a temperature-induced decrease in the molecular weight of the PHA.

The aggregation method of the step (c) according to the invention makes it possible to increase the PHA particle diameter. For example, aggregates with a weight average diameter of not smaller than 10 μm, preferably not smaller than 50 μm, more preferably not smaller than 100 μm, can be obtained. The upper limit is not particularly restricted but aggregates with a weight average diameter of not greater than 5,000 μm, preferably not greater than 3,000 μm, are generally obtained. With the increase in particle diameter, the recovery by filtration becomes easier and the cost of equipment in commercial production can be reduced. The method of filtration is not particularly restricted but, for example, the filtration can be carried out using a filter filtration apparatus, a basket type separator or the like. A more preferred method of recovery is the method comprising recovering the aggregated PHA directly as a dried powder by spray drying, and this method can bring about a reduction in cost of-equipment as compared with the method comprising drying after filtration.

Compositions can be prepared by incorporating, in the PHA obtained in accordance with the present invention, a colorant such as a pigment or dye; a filler such as inorganic or organic particles or grains, glass fiber, whiskers or mica; a stabilizer such as an antioxidant or ultraviolet absorber; and/or another secondary additive such as a lubricant, mold release agent, water repellent or antimicrobial agent, where necessary.

The PHA obtained by the method of the invention and a composition comprising the same can be molded into such shapes as various fibers, yarns, ropes, textiles, knit fabrics, nonwoven fabrics, paper, films, sheets, tubes, plates, bars or rods, containers, bags, parts and foams. They can be formed into biaxially oriented films. The moldings can be appropriately used in the fields of agriculture, fishery, forestry, horticulture, medicine, sanitary goods, clothing, non-clothing, packaging and so forth. Since the PHA obtained by the method of the invention has a high purity, in particular, it is excellent in that it can be adequately utilized in those fields in which such a high purity that can never have been attained by the conventional methods is required, for example in the fields of films, medicine, and sanitary goods.

The method of the invention makes it possible to produce and provide microbial products on a commercial scale and at low cost and, in particular, makes it possible to efficiently recover high-purity PHAs, which have been very difficult to recover by the conventional methods, from PHA-containing microbial cells and thus produce and provide them on a commercial scale and at low cost.

As a result of the induction of autodigestion of nucleic acids by hypochlorous acid treatment of microbial cells in accordance with the invention, the viscosity of the solution in the subsequent step of decomposition or lysis of microbial cells is inhibited from increasing and it becomes easy to recover the intercellular product under relatively mild conditions, so that the microbial product can be produced and provided on a commercial scale and at low cost.

In particular, when the useful substance produced by a microorganism is a polyhydroxyalkanoate, which is a biodegradable polymer, the invention is effective and makes it possible to produce and provide such substance on a commercial scale and at low cost.

BEST MODE FOR CARRYING OUT THE INVENTION

The following examples, in which PHBH was used as the product, further illustrate the product recovery/purification method of the present invention. They are, however, by no means limitative of the scope of the invention.

(Viscosity Evaluation after Treatment with a Hypochlorite)

The viscosity of the aqueous suspension after treatment with a hypochlorite was judged by the eye and evaluated according to the following four-grade criteria:
High: Total gelation;
Medium: Partial gelation;
Low: A slight amount of gel;
None: No gel present.

(Viscosity Measurement)

The viscosity of each cell suspension was measured using a type B viscometer (product of Tokimec Inc.) according to the manual attached thereto.

(Method of Measurement of the Weight Average Molecular Weight of the PHA)

A 10-mg portion of the recovered and dried PHA was dissolved in 5 ml of chloroform, and the insoluble matter was removed by filtration. This solution was analyzed using Shimadzu Corporation's GPC system equipped with Shodex K806L (300×8 mm, two columns coupled; product of Showa Denko K.K.) and using chloroform as the mobile phase. Commercially available standard polystyrene species were used as the molecular weight standard samples. As for the weight average molecular weight of the PHA in microbial cells after completion of cultivation, the PHA was recovered from PHA-containing microbial cells by extraction with chloroform and crystallization from hexane and the measurement was carried out in the same manner, as in the 3HH mole percentage measurement to be mentioned below.

(Method of Measurement of the 3HH Mole Percent and Purity of PHBH)

The PHA (PHBH) in microbial cells after completion of cultivation was recovered by extraction with chloroform and crystallization from hexane and subjected to analysis. The 3HH mole percent was determined by the method described in Example 1 in Japanese Kokai Publication 2001-340078. Thus, 20 mg of PHBH was suspended in 2 ml of a sulfuric acid-methanol mixture (15:85), 2 ml of chloroform was added, and the mixture was heated at 100° C. for 140 minutes. After cooling, 1 ml of distilled water was added and, after stirring, the chloroform layer was recovered. This was analyzed for composition using a Shimadzu Corporation model GC-17A gas chromatograph (with a GL Sciences Neutra Bond column). The total purity of PHBH was determined in the same manner using this method.

(Method of Determining the Protein Content-Based Purity of the PHA)

The PHA (PHBH) recovered was dried at 50° C. under reduced pressure for 5 hours just prior to measurement, and the total nitrogen was determined using a Dia Instruments model TN-10 nitrogen microanalyzer. The nitrogen concentration measured was multiplied herein by 6.38 in calculating the protein content-based purity.

(Particle Size Measurement)

Using a Microtrac particle size analyzer (FRA; product of Nikkiso Co., Ltd.), the aqueous PHA suspension was adjusted to a predetermined concentration and the particle diameter corresponding to the accumulation of 50% of all particles was reported as the average particle diameter of PHA particles.

EXAMPLE 1

Hypochlorite Treatment 1

PHBH was produced by cultivating a strain of R. eutropha with the Aeromonas caviae-derived PHA synthetase group genes introduced therein, which has been internationally deposited as of Aug. 7, 1997 under the name Alcaligenes eutrophus AC32 (accession number: FERM BP-6038), by the method described in Example 1 in Japanese Kokai Publication 2001-340078. After completion of cultivation, microbial cells were recovered by centrifugation, and an aqueous suspension thereof with a dry cell content of 100 g/L was prepared. The recovered microbial cells in the aqueous suspension amounted 10% by weight on the dry weight basis, and the PHBH content in the cells was 60% by weight. To each 50 ml portion of this cell suspension was added 0.1 to 5 ml (0.3 to 14% by weight relative to the dry cell weight) of a sodium hypochlorite solution with an effective chlorine concentration of 12%, as shown in Table 1, and the resulting mixture was stirred at room temperature for 2 hours. After completion of the reaction, the pH was adjusted to 11.7 by addition of 5 N NaOH. In a control run, the hypochlorous acid treatment was not carried out but the alkali treatment alone was carried out. In another control, the cell suspension was subjected to sterilization treatment at 60° C. for 20 minutes, sodium hypochlorite was then added to an effective chlorine concentration of 1.4% by weight in the aqueous suspension, the resulting mixture was stirred at room temperature for 2 hours and, after addition of the alkali, the viscosity was checked.

The viscosity of the solution was estimated by visual observation. The results are shown in Table 1.

TABLE 1

Sodium hypochlorite

| Usage (ml) | Effective chlorine concentration (wt %) per cell suspension (1 mL) | Effective chlorine concentration (wt %) per dry cell weight (g) | pH | Viscosity |
|---|---|---|---|---|
| 0 | 0 | 0 | 6.5 | High |
| 0.1 | 0.03 | 0.3 | 6.5 | Medium |
| 0.25 | 0.07 | 0.7 | 6.5 | Low |
| 0.5 | 0.14 | 1.4 | 6.5 | Low |
| 1.0 | 0.28 | 2.8 | 6.5 | None |
| 2.5 | 0.7 | 7 | 6.6 | None |
| 5.0 | 1.4 | 14 | 6.8 | None |
| 0.5 (Heat sterilization) | 0.14 | 1.4 | 6.5 | High |

As these results indicate, nucleic acid degradation was observed already at an effective chlorine concentration of 0.3% by weight relative to the dry cell weight and, at 0.7% by weight and higher concentrations, almost no increase in viscosity was observed. At 2.8% by weight, nucleic acids were mostly degraded and that concentration was sufficient-for nucleic acid degradation. When the hypochlorous acid treatment was not carried out or when cells were sterilized, the solution became gel-like and no effect of hypochlorous acid was produced.

EXAMPLE 2

Hypochlorite Treatment 2

An 800-ml portion of the same aqueous suspension of cultured cells as used in Example 1 was centrifuged, and 400 ml of the supernatant was discarded to give 400 ml of a twice-concentrated cell suspension (dry cell concentration 20% by weight). To this aqueous suspension of cultured cells was added 8 ml of sodium hypochlorite to an effective chlorine concentration of 1.4% by weight. The pH was 6.5. The mixture was stirred at room temperature for 2 hours and, after completion of the reaction, the pH was adjusted to 8.2 with 5 N NaOH. This aqueous suspension was placed in the cell disrupting vessel 11 shown in FIG. 1, the reaction vessel was connected to a Niro Soavi (Italy) model PA2K high-pressure homogenizer (disrupting apparatus 9), and one homogenization procedure was carried out at a pressure of 400 to 500 kgf/cm$^2$. Then, after each passage of the whole amount of 400 ml, 10% sodium hydroxide was added and, in this manner, the pH of the suspension was adjusted to 10.0, 11.0, 12.5, 12.5 or 12.5 and, after each pH adjustment, the disruption procedure was carried out once. After each disruption procedure, the viscosity of the aqueous suspension was measured. The results are shown in Table 2.

TABLE 2

| pH of aqueous suspension | Viscosity (mPa · s) |
|---|---|
| 6.5 | 10 (Before disruption) |
| 8.2 | 10.3 |
| 10.0 | 12.2 |
| 11.0 | 20.0 |
| 12.5 | 66.5 |

TABLE 2-continued

| pH of aqueous suspension | Viscosity (mPa · s) |
|---|---|
| 12.5 | 27.2 |
| 12.5 | 18.2 |

The viscosity after each disruption was low, and the suspension could be passed through the disrupting apparatus without any problem. The viscosity after disruption at the third pH of 12.5 was 18.2 mPa.s and was almost the same as before disruption.

COMPARATIVE EXAMPLE 1

In Comparative Example 1, cells were disrupted under alkaline conditions without sodium hypochlorite treatment, and the viscosity was checked.

An 800-ml portion of the same aqueous suspension of cultured cells as used in Example 1, which had a dry cell concentration of 10% by weight, was placed in the cell disrupting vessel 11 and adjusted to pH 9.1 with 10% NaOH. The reaction vessel was connected to a Niro Soavi (Italy) model PA2K high-pressure homogenizer (disrupting apparatus 9), and one disruption procedure was carried out at a pressure of 400 to 500 kgf/cm$^2$. The viscosity after completion of this disruption was 123 mPa.s. The pH was further adjusted to 11.0 and the disruption procedure was carried out, upon which the viscosity abruptly rose to 1,325 mPa.s and a gel partially clung to the agitating shaft, producing a problem in introduction into the disrupting apparatus. Eleven repetitions of disruption were required until the viscosity became 30 mPa.s.

EXAMPLE 3

In Example 3, the pH was made alkaline at an early stage after hypochlorous acid treatment, and the extent of decrease in the molecular weight of PHBH was checked. Further, an enzyme/surfactant treatment was carried out, and the quality after washing with water was evaluated.

Figure 2:
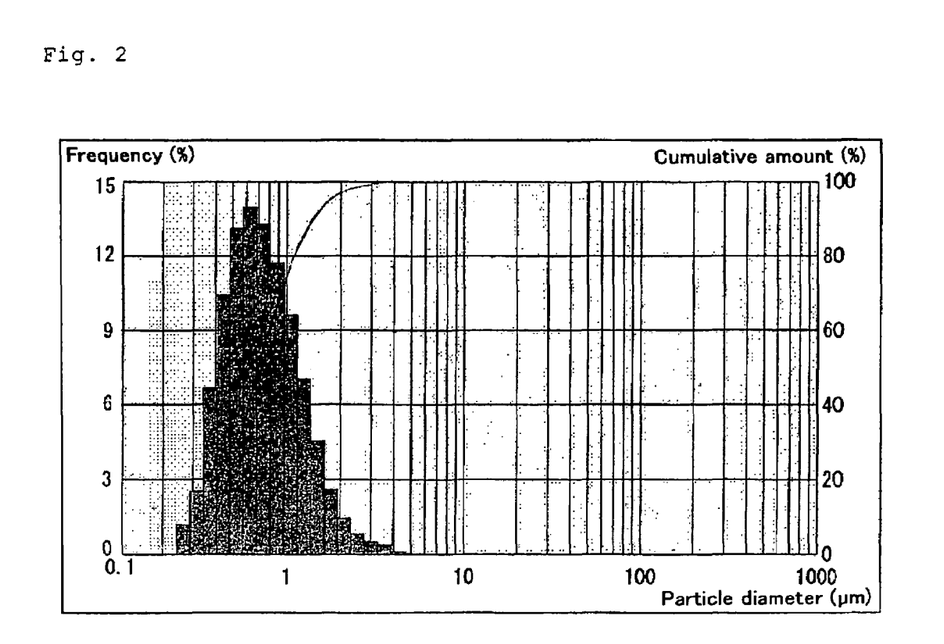
FIG. 2 is a graphic representation of the results of particle size analysis of the PHA particles obtained in Example 3.

PHBH was produced by cultivating a strain of *R. eutropha* with the *Aeromonas caviae*-derived PHA synthetase group genes introduced therein, which has been internationally deposited as of Aug. 7, 1997 under the name *Alcaligenes eutrophus* AC32 (accession number: FERM BP-6038), by the method described in Example 1 in Japanese Kokai Publication 2001-340078. After completion of the cultivation, the cell content was 9.9% by weight, the weight average molecular weight was 2,070,000, the polymer content was 62% by weight, the 3HH content was 4.5 mole percent. To this culture broth (1.2 L) was added 12 ml of a sodium hypochlorite solution (effective chlorine concentration 1.4% by weight), and the mixture was stirred at 30° C. for 2 hours. The pH was 6.5. After completion of the reaction, centrifugation (8,000 rpm, 20 minutes) was carried out, and 0.6 L of the supernatant was removed. The remaining cell suspension (20% by weight on the dry cell basis) was adjusted to pH 8.0 with 10% sodium hydroxide, and one high-pressure disruption procedure was carried out at 400 to 500 kg/cm$^2$. Then, the pH was adjusted to 12.5 at a stretch and, while maintaining this pH, the high-pressure disruption was carried out five times. After each disruption procedure, the viscosity, the protein content-based purity, the total purity of PHBH and the weight average molecular weight thereof were measured. The viscosity increased just after adjustment to pH 12.5 but the disruption could be continued without any problem. After each disruption, sampling is performed and the polymer was recovered by centrifugation and washed with water by newly adding water, followed by stirring and centrifugation. Water (15.8 g) was added to the washed polymer for suspending the same. To each sample thus obtained were added 0.02 g of Esperase (Alcalase; product of Novozymes A/S) and 0.125 g of a surfactant (AC3S, The Stephan Company), and the enzyme/surfactant treatment was carried out at 40° C. for 1 hour. The sample was washed with 4 portions of water. At this point of time, the particle size of the polymer was measured and the polymer was found to occur as an emulsion comprising fine particles with an average particle size of 0.7 microns (FIG. 2). This emulsion was washed with two portions of ethanol, and the polymer was then recovered by centrifugation and dried at 50° C. for 6 hours under reduced pressure. The nitrogen content of the polymer obtained was measured. The results are shown in Table 3.

TABLE 3

| Sample | Viscosity (mPa · s) | Weight average molecular weight | % Purity (protein-based) |
| --- | --- | --- | --- |
| Starting material (after completion of cultivation) | 9 | 2,074,830 | — |
| After 2 hours of stirring following addition of hypochlorous acid | 9 | 2,126,190 | — |
| Before disruption | 9 | — | — |
| After 1 disruption at pH 8 | 103 | 2,177,580 | 96.1 |
| After adjustment to pH 12.5 | 123 | 2,206,980 | — |
| After 1 disruption at pH 12.5 | 76 | 2,134,380 | 98.0 |
| After 2 disruptions at pH 12.5 | 50 | 2,191,850 | 98.1 |
| After 3 disruptions at pH 12.5 | 45 | 2,175,270 | 98.5 |
| After 4 disruptions at pH 12.5 | 28 | 2,208,770 | 99.1 |
| After 5 disruptions at pH 12.5 | 28 | 2,207,250 | 99.3 |

As a result, no decrease in molecular weight was found at each pH, the purity based on the protein content was 99.3% and the total purity was 98%; a satisfactory product was thus obtained. From the above results, it could be confirmed that the sodium hypochlorite treatment of viable cells is effective in reducing the viscosity during disruption, that the PHA obtained does not show any substance decrease in molecular weight, and that the quality of the PHA is on the whole good.

EXAMPLE 4

The particle size of PHBH was caused to increase by aggregation and then the PHBH was recovered.

The polymer after washing with ethanol as obtained in the same manner as in Example 3 was made into an aqueous suspension (200 g/L). To the suspension was added 280 ml of 95% ethanol, and the resulting suspension was then subjected to centrifugation to precipitate PHBH. A 280-ml portion of the supernatant was removed, and 280 ml of 95% ethanol was again added to the polymer fraction to suspend the PHBH. This ethanol washing was repeated twice in total and then 280 ml of 95% ethanol was added to give a suspension. The PHBH suspension was gradually added to 290 ml of 95% ethanol at 70° C. over 15 minutes, the resulting mixture was stirred for 10 minutes following completion of the addition to allow the PHBH to aggregate. The PHBH aggregate was recovered by filtration. The PHBH was washed with two 120-ml portions (each portion being equal in volume to the volume of PHBH) of 95% ethanol on the filter. The PHBH aggregate obtained was dried at 50° C. under vacuum. Thus was obtained 65 g (recovery rate 93%) of PHBH with a protein content-based purity of 99.9% and a total purity of 99%. The polymer aggregate had a particle size of 50 μm. The weight average molecular weight was 1,970,000, indicating only a 5% reduction after completion of the cultivation.

The invention claimed is:

1. A method of recovering a product which comprises, in the step of recovering a substance produced by a microorganism from within microbial cells, bringing living microbial cells into contact with an amount appropriate for induction of autodigestion of nucleic acids of hypochlorous acid or a salt thereof and then carrying out the step of product recovery, wherein the microbial cells are brought into contact with hypochlorous acid or a salt thereof at a temperature of 15 to 40° C. and a pH of 4 to 7.

2. The method of recovering a product according to claim 1, wherein the concentration of hypochlorous acid or a salt thereof for inducing autodigestion of nucleic acids in microbial cells, as expressed in terms of effective chlorine concentration, is 0.3% by weight to 14% by weight relative to the dry weight of cells.

3. The method of recovering a product according to claim 1, wherein the microbial product is a polyhydroxyalkanoate, which is a biodegradable polymer.

4. The method of recovering a product according to claim 3, wherein the polyhydroxyalkanoate is a copolymer resulting from copolymerization of at least two monomers selected from the group consisting of 3-hydroxybutyrate, 3-hydroxyvalerate, 3-hydroxypropionate, 4-hydroxybutyrate, 4-hydroxyvalerate, 5-hydroxyvalerate, 3-hydroxyhexanoate, 3-hydroxyheptanoate, 3-hydoxyoctanoate, 3-hydroxynonanoate and 3-hydroxydecanoate.

5. The method of recovering a product according to claim 3, wherein the polyhydroxyalkanoate is a copolymer of 3-hydroxyhexanoate and at least one of other hydroxyalkanoates.

6. The method of recovering a product according to claim 3, wherein the polyhydroxyalkanoate is a copolymer of 3-hydroxyhexanoate and 3-hydroxybutyrate.

7. The method of recovering a product according to claim 1, wherein the microorganism is a polyhydroxyalkanoate-containing microorganism selected from the group consisting of microorganisms of the genera Aeromonas, Alcaligenes, Azotobacter, Bacillus, Candida, Clostridium, Halobacterium, Nocardia, Rhodospinlium, Pseudomonas, Ralstonia, Saccharomyces, Yarrowia, Zoogloea, Methylobacterium, and Paracoccus.

8. The method of recovering a product according to claim 1, wherein the microorganism is *Aeromonas caviae*.

9. The method of recovering a product according to claim 1, wherein the microorganism is a transformant with the *Aeromonas caviae*-derived polyhydroxyalkanoate synthetase group genes introduced therein.

10. The method of recovering a product according to claim 9, wherein the microorganism is *Ralstonia eutropha* with the *Aeromonas caviae*-derived polyhydroxyalkanoate synthetase group genes introduced therein.

11. The method of recovering a product according to claim 3,
wherein the product recovery process to be carried out after bringing living cells with an amount appropriate for inducing autodigestion of nucleic acids of hypochlorous acid or a salt thereof comprises the following steps (a) and (b):
(a) the step of adding an alkali to an aqueous suspension of polyhydroxyalkanoate-containing microbial cells while stirring and carrying out a physical disruption treatment to thereby disrupt the cells and, at the same time, solubilize or emulsify cell substances other than the polyhydroxyalkanoate in those cells and then separating the polyhydroxyalkanoate from the suspension;
(b) the step of treating the polyhydroxyalkanoate separated with an enzyme and/or a surfactant to solubilize, or digest/decompose and then solubilize, impurities adhering to the polyhydroxyalkanoate and then washing the polyhydroxyalkanoate with a hydrophilic solvent and/or water.

12. The method of recovering a product according to claim 11
which further comprises the following step (c):
(c) the step consisting in suspending the washed polyhydroxyalkanoate in a hydrophilic solvent and/or water, stirring the suspension at a temperature not higher than the boiling point of the suspension to allow the polyhydroxyalkanoate to aggregate to an increased particle size and then separating the polyhydroxyalkanoate after aggregation from the suspension.

13. The method of recovering a product according to claim 11,
wherein, in the step (a), the physical disruption treatment is carried out using a high-pressure homogenizer.

14. The method of recovering a product according to claim 11,
wherein, in the step (a), the physical disruption is carried out while controlling the pH of the aqueous suspension within the range of 9 to 13.5.

15. The method of recovering a product according to claim 11,
wherein the alkali used in the step (a) is at least one species selected from the group consisting of sodium hydroxide, potassium hydroxide, lithium hydroxide and sodium carbonate.

16. The method of recovering a product according to claim 11,
wherein the enzyme used in the step (b) is at least one species selected from the group consisting of proteases, fatty acid decomposing enzymes, cell wall decomposing enzymes and nucleases.

17. The method of recovering a product according to claim 11,
wherein the surfactant used in the step (b) is at least one species selected from the group consisting of anionic surfactants, cationic surfactants, amphoteric surfactants and nonionic surfactants.

18. The method of recovering a product according to claim 11,
wherein the hydrophilic solvent used for washing in the step (b) is at least one species selected from the group consisting of methanol, ethanol, propanol, isopropanol, acetone, acetonitrile and tetrahydrofuran.

19. The method of recovering a product according to claim 12,
wherein the hydrophilic solvent used in the step (c) is at least one species selected from the group consisting of methanol, ethanol, propanol, isopropanol, acetone, acetonitrile and tetrahydrofuran.

20. The method of recovering a product according to claim 11,
wherein the polyhydroxyalkanoate obtained after the step (a) or step (b) is recovered in the form of an emulsion.

21. The method of recovering a product according to claim 11,
wherein the polyhydroxyalkanoate obtained after the step (c) is recovered in the form of a dry powder by spray drying.

22. The method of recovering a product according to claim 1,
wherein the salt of hypochlorous acid is sodium hypochlorite.

* * * * *

UNITED STATES PATENT AND TRADEMARK OFFICE
CERTIFICATE OF CORRECTION

| | |
|---|---|
| PATENT NO. | : 7,435,567 B2 |
| APPLICATION NO. | : 11/070083 |
| DATED | : October 14, 2008 |
| INVENTOR(S) | : Fumio Osakada et al. |

Page 1 of 1

It is certified that error appears in the above-identified patent and that said Letters Patent is hereby corrected as shown below:

In Claim 7
Line 7, change "Rhodospinlium" to --Rhodospirillum--

Signed and Sealed this

Twenty-fourth Day of March, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,435,567 B2 Page 1 of 1
APPLICATION NO. : 11/070083
DATED : October 14, 2008
INVENTOR(S) : Fumio Osakada et al.

It is certified that error appears in the above-identified patent and that said Letters Patent is hereby corrected as shown below:

Column 20, In Claim 7
Line 52, change "Rhodospinlium" to --Rhodospirillum--

This certificate supersedes the Certificate of Correction issued March 24, 2009.

Signed and Sealed this

Fourteenth Day of April, 2009

JOHN DOLL
*Acting Director of the United States Patent and Trademark Office*